US007252685B2

(12) United States Patent
Bindseil et al.

(10) Patent No.: US 7,252,685 B2
(45) Date of Patent: Aug. 7, 2007

(54) FUSION IMPLANT AND METHOD OF MAKING SAME

(75) Inventors: James J. Bindseil, Germantown, TN (US); William F. McKay, Memphis, TN (US); Cary R. Reeves, Aledo, TX (US); T. Andrew Simonton, Memphis, TN (US); Eddie F. Ray, Collierville, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 0 days.

(21) Appl. No.: 10/455,760

(22) Filed: Jun. 5, 2003

(65) Prior Publication Data

US 2004/0249471 A1    Dec. 9, 2004

(51) Int. Cl.
A61F 2/28 (2006.01)
A61F 2/44 (2006.01)
A61B 17/56 (2006.01)
A61K 6/083 (2006.01)

(52) U.S. Cl. ............................... 623/16.11; 623/17.11; 606/76; 427/2.26

(58) Field of Classification Search ............. 623/16.11, 623/23.51, 23.52, 23.54, 17.11–17.16, 23.61, 623/23.64; 424/422–426; 427/2.26, 2.27
See application file for complete search history.

(56) References Cited

U.S. PATENT DOCUMENTS

| 4,787,906 A * | 11/1988 | Haris ........................ 623/23.72 |
| 4,839,215 A | 6/1989 | Starling et al. ............... 428/131 |
| 4,950,296 A | 8/1990 | McIntyre ..................... 623/16 |
| 5,298,254 A * | 3/1994 | Prewett et al. ............... 424/422 |
| 5,306,304 A * | 4/1994 | Gendler ..................... 623/23.63 |
| 5,507,813 A | 4/1996 | Dowd et al. .................. 623/16 |
| 5,549,679 A * | 8/1996 | Kuslich ..................... 623/17.12 |
| 5,571,189 A | 11/1996 | Kuslich ........................ 623/17 |
| 5,571,190 A | 11/1996 | Ulrich et al. .................. 623/17 |
| 5,676,146 A | 10/1997 | Scarborough ................ 128/654 |
| 5,895,426 A | 4/1999 | Scarborough et al. ......... 623/17 |
| 5,899,939 A | 5/1999 | Boyce et al. .................. 623/16 |
| 6,025,538 A | 2/2000 | Yaccarino ..................... 623/16 |
| 6,090,998 A | 7/2000 | Grooms et al. ................ 623/16 |
| 6,123,731 A * | 9/2000 | Boyce et al. ............. 623/23.63 |
| 6,146,420 A | 11/2000 | McKay ........................ 623/17 |
| 6,200,347 B1 | 3/2001 | Anderson et al. ......... 623/16.11 |
| 6,270,528 B1 | 8/2001 | McKay ..................... 623/17.11 |
| 6,294,041 B1 | 9/2001 | Boyce et al. ............. 156/275.5 |
| 6,315,795 B1 | 11/2001 | Scarborough et al. ...... 623/7.11 |
| 6,371,988 B1 | 4/2002 | Pafford et al. ............ 623/17.11 |
| 6,379,385 B1 | 4/2002 | Kalas et al. ............... 623/17.11 |
| 6,409,765 B1 | 6/2002 | Bianchi et al. ............ 623/17.11 |
| 6,458,158 B1 | 10/2002 | Anderson et al. ......... 623/16.11 |
| 6,468,311 B2 | 10/2002 | Boyd et al. ............... 623/17.16 |

(Continued)

FOREIGN PATENT DOCUMENTS

WO    WO 99/29271    6/1999

(Continued)

*Primary Examiner*—David J. Isabella
(74) *Attorney, Agent, or Firm*—Woodard, Emhardt, Moriarty, McNett & Henry LLP (57) ABSTRACT

The present invention provides an implant for use in fusing adjacent bony structures. The implant comprises at least one structural member combined with at least one flexible planar member to retain the at least one structural member to form the implant.

73 Claims, 3 Drawing Sheets

U.S. PATENT DOCUMENTS

| | | | |
|---|---|---|---|
| 6,478,822 B1 * | 11/2002 | Leroux et al. | 623/17.14 |
| 6,503,277 B2 | 1/2003 | Bonutti | 623/11.11 |
| 6,620,196 B1 * | 9/2003 | Trieu | 623/17.16 |
| 6,679,914 B1 * | 1/2004 | Gabbay | 623/14.12 |
| 6,758,863 B2 * | 7/2004 | Estes et al. | 623/17.16 |
| 2001/0020186 A1 | 9/2001 | Boyce et al. | 623/17.16 |
| 2001/0031254 A1 | 10/2001 | Bianchi et al. | 424/93.7 |
| 2001/0032017 A1 | 10/2001 | Alfaro et al. | 623/17.11 |
| 2001/0039456 A1 | 11/2001 | Boyer et al. | 623/23.52 |
| 2001/0039457 A1 | 11/2001 | Boyer et al. | 623/23.52 |
| 2001/0039458 A1 | 11/2001 | Boyer et al. | 623/23.63 |
| 2001/0041941 A1 | 11/2001 | Boyer et al. | 623/23.52 |
| 2001/0049560 A1 | 12/2001 | Paul et al. | 623/17.16 |
| 2001/0056302 A1 | 12/2001 | Boyer et al. | 623/17.15 |
| 2002/0029082 A1 | 3/2002 | Muhanna | 623/17.11 |
| 2002/0029084 A1 | 3/2002 | Paul et al. | 623/23.63 |
| 2002/0045944 A1 | 4/2002 | Muhanna et al. | 623/17.16 |
| 2002/0062153 A1 | 5/2002 | Paul et al. | 623/17.11 |
| 2002/0082693 A1 | 6/2002 | Ahlgren | 623/17.11 |
| 2002/0091447 A1 | 7/2002 | Shimp et al. | 623/17.16 |
| 2002/0165612 A1 | 11/2002 | Gerber et al. | 623/17.11 |
| 2003/0045934 A1 | 3/2003 | Bonutti | 623/11.11 |
| 2003/0050708 A1 | 3/2003 | Bonutti | 623/23.57 |

FOREIGN PATENT DOCUMENTS

| | | |
|---|---|---|
| WO | WO 00/30568 | 6/2000 |
| WO | WO 01/49220 | 7/2001 |
| WO | WO 01/66048 | 9/2001 |
| WO | WO 01/70136 | 9/2001 |
| WO | WO 01/78798 | 10/2001 |
| WO | WO 02/24233 | 3/2002 |
| WO | WO 02/056800 A2 | 7/2002 |
| WO | WO 02/064180 | 8/2002 |
| WO | WO 02/065957 | 8/2002 |
| WO | WO 02/098329 | 12/2002 |
| WO | WO 02/098332 | 12/2002 |

* cited by examiner

FUSION IMPLANT AND METHOD OF MAKING SAME

BACKGROUND

Implants for use in fusing adjacent bony structures facilitate fusion by maintaining the adjacent bony structures in a predetermined spaced relationship while bone grows between them. In some cases these implants are formed from body tissues. In forming an implant from body tissue, a source of tissue, such as a bone, is formed into pieces meeting the desired shape and strength requirements for a particular implant. In the case of bone, the requirements are often specified in terms of a minimum wall thickness, minimum load bearing capacity, and/or geometric size and shape. A portion of the source tissue, including pieces removed in forming implants, will fall short of the requirements to form an integral implant. Thus, it is often difficult to obtain a high yield from a particular source.

SUMMARY

The present invention provides an implant for use in fusing adjacent bony structures.

In one aspect of the invention, an implant for use in fusing adjacent bony structures comprises at least one structural member combined with at least one flexible planar member to retain the at least one structural member to form the implant.

In another aspect of the invention, a load bearing implant for use in fusing adjacent bony structures comprises a plurality of bone pieces and a flexible planar member containing the bone pieces to give a predetermined form to the implant.

In another aspect of the invention, a load bearing implant for use in fusing adjacent bony structures comprises a plurality of bone pieces and a flexible planar member, the bone pieces and flexible planar member forming alternating layers.

In another aspect of the invention, a load bearing implant for use in fusing adjacent bony structures comprises a plurality of layers comprising a flexible planar member and at least one structural member extending through at least two of the plurality of layers to affix the at least one structural member at a predetermined orientation within the layers.

In another aspect of the invention, a load bearing implant for use in fusing adjacent bony structures comprises load bearing means for supporting said adjacent bony structure in spaced relationship and retaining means for retaining the load bearing means in a predetermined orientation.

In another aspect of the invention, a method of treating a body to promote fusion of adjacent bony structures comprises the steps of providing a plurality of bone pieces; containing the plurality of bone pieces in a flexible planar member to form an implant having a predetermined form; and placing the implant between adjacent bony structures.

In another aspect of the invention, a system for use in fusing adjacent bony structures comprises a plurality of bone pieces; at least one flexible planar member substantially retaining the plurality of bone pieces; and a fixation device attachable to the adjacent bony structures and having a structure to limit relative motion between the adjacent bony structures.

In another aspect of the invention, an implant for use in fusing adjacent bony structures comprises at least one retaining member having a first load carrying capacity and at least one structural member having a second load carrying capacity greater than the first, the retaining member retaining the structural member in a predetermined orientation relative to the adjacent bony structures.

BRIEF DESCRIPTION OF THE DRAWINGS

Various embodiments of the present invention will be discussed with reference to the appended drawings. These drawings depict only illustrative embodiments of the invention and are not to be considered limiting of its scope.

DETAILED DESCRIPTION

Embodiments of a bone fusion implant include one or more structural members and one or more flexible planar members to retain the structural members to form a load-bearing implant for use in fusing adjacent bony structures. The adjacent bony structures may include vertebrae, long bones, and cranial bones, among others. The flexible planar member may retain a plurality of structural members in a predetermined form, spacing, and/or orientation. For example, the flexible planar member may enclose the structural members and retain them in a rectangular, hemispherical, cylindrical, or other suitable form. In this way, structural members that individually fail to meet strength and/or geometry requirements can be massed together to meet the requirements. Furthermore, the flexible planar member may retain one or more structural members in a predetermined spacing or orientation. For example, the flexible planar member may retain an elongate structural member such that its axis is in a predetermined load bearing orientation relative to the adjacent bone tissues. For example, one or more structural members may meet the load bearing requirement for a particular application but may not be large enough to fill the space between adjacent bony structures and/or remain properly oriented. The flexible planar member may retain them and keep them from moving out of position. The structural member may have a load bearing capacity greater than the load bearing capacity of the flexible planar member. While the flexible planar member retains the structural members, the combination may be sufficiently flexible in one or more dimensions to conform to surrounding body tissues. For example, the combination may conform to the shape defined by the annulus fibrosus of a spinal disc.

The flexible planar member may comprise a biocompatible, flexible structure capable of retaining structural members. The flexible planar member may include one, more than one, or combinations of different types of elongated, planar material including natural and man-made materials. The flexible planar member may be in the form of a sheet, block, foam, woven fabric, non-woven fabric, mesh, membrane, and/or other suitable flexible form and combinations thereof. The flexible planar member may comprise a cellular scaffold such as, for example, one made of cellulose including carboxy methyl cellulose. The flexible planar member may be made of body tissue, resorbable polymers, nonresorbable polymers, metals, and/or other suitable materials and combinations thereof. A flexible planar member including body tissue may include fascia, skin, pericardium, partially demineralized bone, fully demineralized bone, annulus fibrosis, cartilage, tendon, ligament, and/or other suitable body tissues and combinations thereof. A flexible planar member including polymers may include polyethylene, polyester, polyglycolic acid, polylactic acid, polyaryletherketone, polyetheretherketone, polytetrafluroethylene, and/or other suitable polymers and combinations thereof. Depending on the application and the loads that may be applied to the fusion implant, one type of flexible planar member may be utilized in one dimension while a different type of flexible planar member may be utilized in another dimension. Additionally, the flexible planar member may include one or more openings to facilitate fusion of adjacent bony structures. For example, the one or more openings may be sized such that they are smaller than the structural members such that they may be contained by the flexible planar member. Alternately, a retaining material such as bone paste, collagen, gelatin, polymers, and/or other suitable material may be inserted within the one or more openings to bind with one or more structural members to retain them within the one or more openings. Further, the flexible planar member may be wrapped around or positioned adjacent to the structural members to form the fusion implant.

The structural members may include any form and any biocompatible material capable of withstanding a predetermined load. The structural member may be in the form of particles, strips or sticks, blocks, or beams. For example, a beam may have a cross sectional shape that is round, rectangular, "I"-shaped, "T"-shaped, "C"-shaped or other suitable shape. The structural member may be may be made from bone, metal, ceramic, carbon, and/or polymers and combinations thereof. If it is of bone, each piece of bone may comprise cortical bone for achieving a predetermined load-bearing capability in the implant. Additionally, each piece or strip of bone may comprise cancellous bone. Further, the pieces of bone may be mineralized, partially demineralized, fully demineralized, or combinations thereof. If the structural member includes polymers, they may be resorbable or non-resorbable and include polyethylene, polyester, polyglycolic acid, polylactic acid, polyaryletherketone, polyetheretherketone, polytetrafluroethylene, and/or other suitable polymers and combinations thereof.

In an implant having structural members including pieces of bone, the flexible planar member retains the bone pieces to form the bone fusion implant. Thus, combining a plurality of bone pieces into an implant retained by a flexible planar member allows donor bone having less than a predetermined minimum load bearing capacity and/or a predetermined geometry outside of a predetermined standard to be combined to form an assembled bone load-bearing implant that achieves the predetermined capacity and/or geometry. The shape and size distribution of the pieces may be determined in accordance with granular mechanics to further impart shape retention, load bearing capacity, and/or stability to the implant. Likewise, orienting one or more bone pieces in a predetermined load bearing orientation permits the use of bone pieces that would not otherwise be large enough to fill the space between adjacent bony structures and/or remain properly oriented.

The bone pieces may have any suitable length, width and height, and any geometry. For example, each bone piece may have a predetermined cortical bone thickness and/or geometry that is less than a predetermined minimum thickness and/or geometry for an integral or multi-piece load-bearing bone implant.

Figure 1:
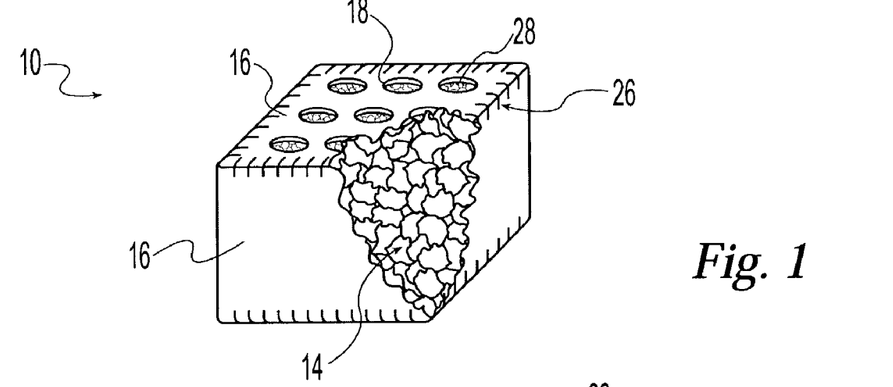
FIG. 1 is a perspective view of an illustrative implant according to the present invention with a portion of the outer member shown in broken line to reveal the inner structure of the embodiment.
Figure 2:
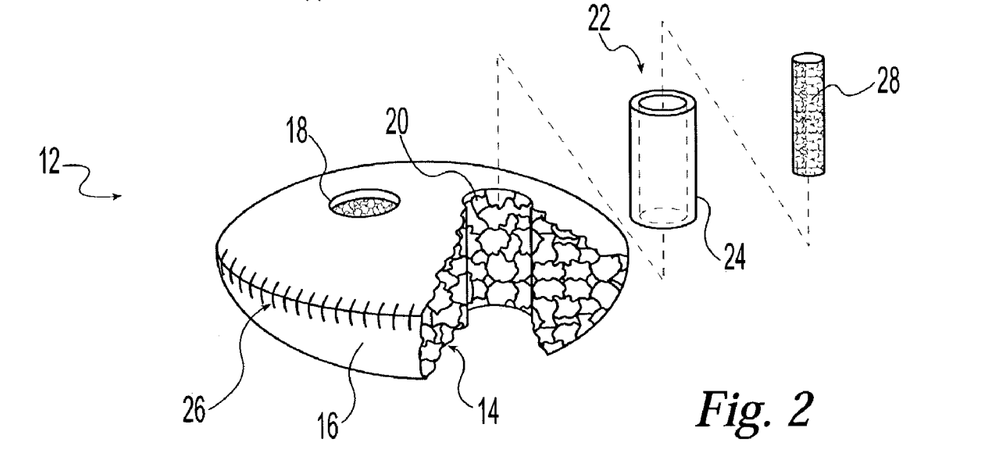
FIG. 2 is a perspective view of an implant similar to that of FIG. 1 showing an alternative shape and hollow member.

Referring to FIGS. 1 and 2, illustrative embodiments of a fusion implant 10, 12 include structural members comprising a plurality of bone pieces 14 held in a predetermined form by one or more flexible planar members 16. The predetermined form may be any form suitable for achieving bone fusion between adjacent bony structures. For example, one fusion implant 10 (FIG. 1) includes substantially rectangular dimensions, while the other fusion implant 12 (FIG. 2) includes partially hemispherical surfaces and disc-like dimensions. The fusion implant 10, 12 may be placed between adjacent bony structures to maintain the bony structures in spaced relationship and promote fusion of the bony structures. The bony structures may be prepared to receive the implant such as by chiseling, reaming, abrading, or sawing the bones to conform to the shape of the implant and/or to expose underlying bone tissues. The flexible planar member may allow the implant to conform to the shape of the bony structures. The partially hemispherical implant 12 may be shaped to fit the natural contour of adjacent bony structures such as the endplates of adjacent vertebral bodies. The implant shape may be determined by the configuration of the one or more planar members, or a mold, a press, or any other type of shaping device may be utilized to assemble the implants 10, 12 into the predetermined form.

The plurality of bone 14 may be pieces of any size, shape or combinations of different sized and shaped pieces. Each of the plurality of bone pieces 14 may be independent of adjacent bone pieces, or the pieces may be interconnected or joined, such as through mechanical or chemical mechanisms, e.g. pinning, suturing, pressing, incorporating a binding agent, collagen crosslinking, entangling, and other suitable means and combinations thereof.

If the pieces are pinned, holes may be formed in the pieces and rigid pins made of bone, ceramic, metal, polymers, and/or other suitable materials may be pressed into the holes to interconnect the pieces.

If the pieces are sutured together, holes may be formed in the pieces and a flexible, elongate, biocompatible connector may be threaded through the holes to interconnect the pieces. The connector may be a suture and/or elongate pieces of body tissue. Examples of materials for such connectors include pericardium, demineralized bone, fascia, cartilage, tendon, ligament, skin, collagen, elastin, reticulum, intestinal submucosa, metal, resorbable polymer, and nonresorbable polymer, and/or other suitable material.

If a binding agent is used to interconnect the pieces, it may be an adhesive binding agent, a cementitious binding agent, and/or other suitable binding agent. Examples of adhesive binding agents include fibrin glue, cyanoacrylate, epoxy, polymethylmethacrylate, gelatin based adhesives, and other suitable adhesives and combinations thereof. Examples of cementitious binding agents include settable ceramics, calcium carbonate, calcium phosphate, plaster, and other suitable materials and combinations thereof.

If the pieces are interconnected by collagen cross-linking, the bone pieces may be partially demineralized to expose collagen fibers which may then be crosslinked by application of heat, pressure, chemicals, and/or other suitable cross-linking means.

The one or more flexible planar members 16 may entirely encompass the plurality of bone pieces 14 to retain the bone in any predetermined form. Alternately, there may be predetermined openings 18 within the flexible planar member to allow exposure of the plurality of bone pieces 14 to bony structures adjacent to the fusion implant 10, 12. The predetermined openings 18 may include predetermined spacing between portions of the one or more planar members 16, or may include openings formed within the one or more planar members. Further, referring to FIG. 2, one or more of the predetermined openings 18 may comprise an inner wall 20 extending through the entire implant 12. The inner wall 20 may be formed through one or more flexible planar members and through the plurality of bone pieces 14. For example, the opening 18 and inner wall 20 (FIG. 2) may be formed by, but not limited to, any form of drilling, cutting, or punching type of operation. Alternately, the opening 18 and inner wall 20 may be formed around a hollow member 22 having a wall 24 defining the opening 18 and inner wall 20. Suitable examples of a hollow member 22 include any biocompatible material capable of preventing the passage of the bone pieces through its structure, such as a polymeric material, a bone material, or any biocompatible structure. The hollow member 22 may be positioned within the implant at any time, such as after an opening is formed, or may be positioned within the bone 14 and flexible planar member 16 as the implant is being formed. Additionally, fusion implant 10, 12 may include a securing mechanism 26 to insure that the one or more planar members 16 maintain a bone-retaining position. The securing mechanism 26 may attach one portion of a planar member 16 to another portion of the planar member, and/or it may secure one planar member to another planar member and/or to surrounding bone. Suitable examples of a securing mechanism 26 include heat bonding, cross-linking, adhesive bonding, chemical bonding, ultrasonic welding, biocompatible sutures, wires, pins, straps, clamps, and/or any other mechanism capable of fixing a flexible planar member in a predetermined relationship relative to itself, another flexible planar member, and/or relative to the plurality of bone pieces. The securing mechanism 26, as well as the flexible planar member 16 may also comprise a material that resorbs within the body after a predetermined period of time. In another alternative embodiment, a bone growth-promoting material 28, such as bone paste, cancellous bone, bone chips, bone morphogenic protein (BMP), LIM mineralization protein (LMP), platelet derived growth factors, bone marrow aspirate, stem cells, biologic growth factors, and/or other suitable materials and combinations thereof, may be inserted within openings 18 to aid in fusing adjacent bony masses and/or to secure the plurality of bone pieces 14 to each other adjacent the openings to aid in keeping the bone within the flexible planar member 16. Additionally, a plurality of implants 10, 12 may be attached via securing mechanism 26 to form a larger implant.

Figure 3:
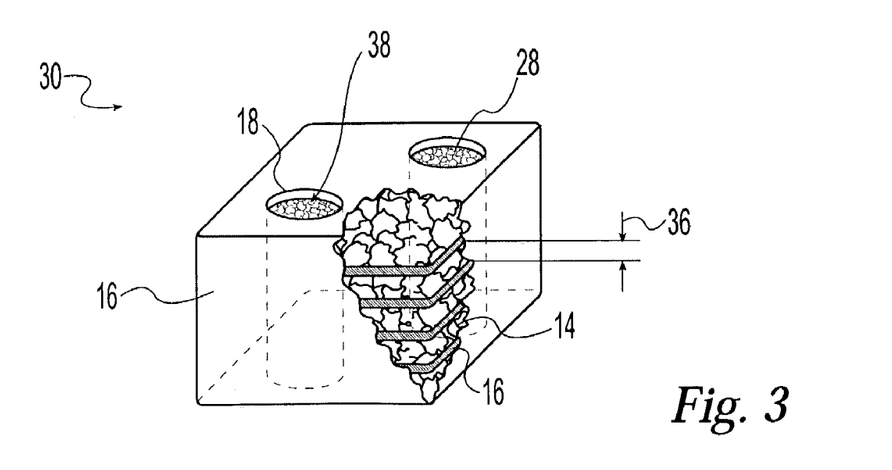
FIG. 3 is a perspective view of an implant similar to that of FIG. 1 showing an alternative construction of stacked layers.
Figure 4:
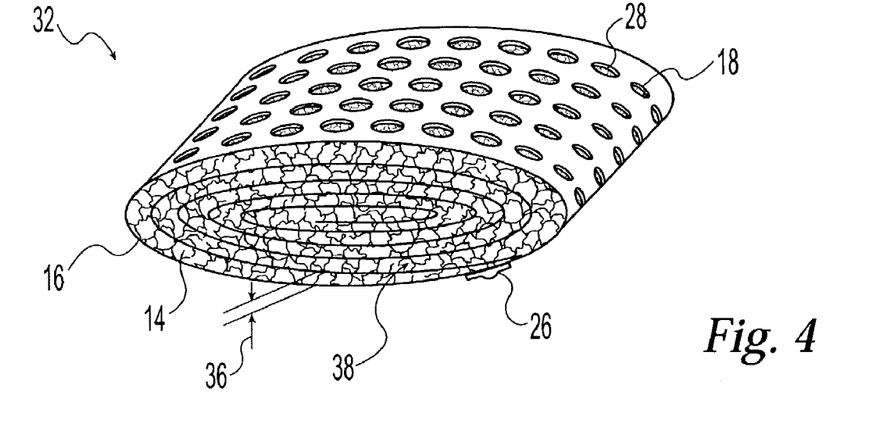
FIG. 4 is a perspective view of an implant like that of FIG. 1 showing an alternative construction of spirally rolled layers.
Figure 5:
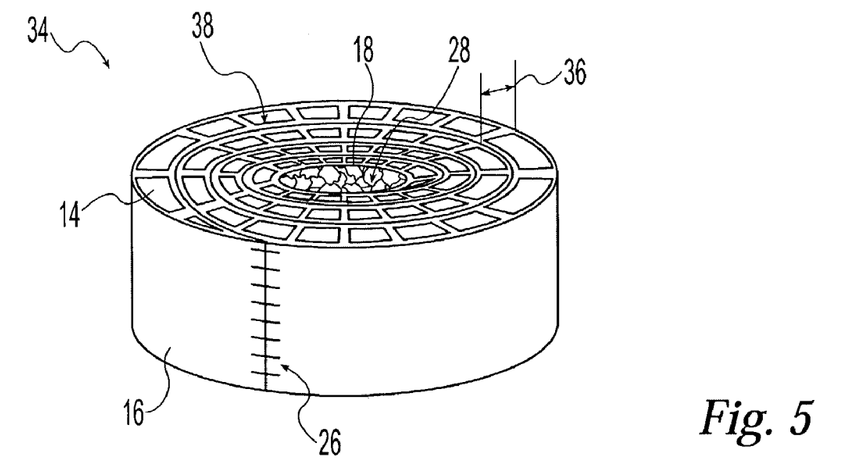
FIG. 5 is a perspective view of an implant like that of FIG. 4 showing another type of spirally rolled layer construction.
Figure 6:
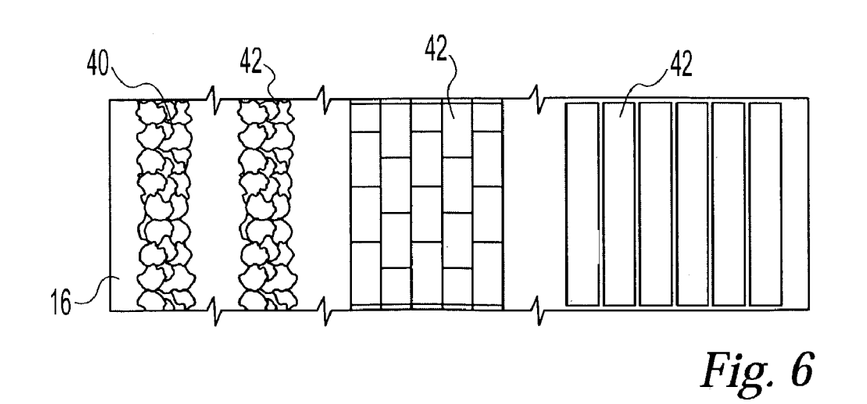
FIG. 6 is a plan view of the illustrative embodiment of FIG. 5 prior to it being rolled.

Referring to FIGS. 3-5, other embodiments of a fusion implant 30, 32, 34 include the structural members comprising a plurality of bone pieces 14 and one or more flexible planar members 16 positioned in one or more layers 36 to form the respective implant 30, 32, 34. Implants 30, 32, 34 may include layers 36 of any orientation, such as substantially horizontal, substantially vertical, substantially curvilinear, substantially planar, and/or other suitable orientation. Some layers 36 may be designed primarily as structural layers, such as by including cortical bone, while other layers may be designed as fusion layers, such as by including cancellous bone or other bone growth promoting materials, and other layers may be combinations of both. Layered implants 30, 32, 34 may have exposed bone 14 at an edge 38 or other portion of one or more layers 36. Such exposed bone 14 at an edge 38 would promote fusion of adjacent bony structures through the layer and/or through the implant. Alternately, a flexible planar member 16 may cover the exposed bone 14 at one or more edges 38. Further, the plurality of layers 36 may be formed such as by rolling, stacking or otherwise aligning a single layer to form multiple layers. Referring to FIG. 6, for example, a fusion implant may be formed by placing structural members onto one or more flexible planar members 16 and then rolling them up to form a radially layered implant. In the illustrative embodiment, structural members having different forms and composition are combined including cancellous bone pieces in particle form 40, and cortical bone pieces 42 in particle, block, and beam form. Additionally, a bone growth promoting material 28 may be included within the implant. In the illustrative embodiment, cancellous material is placed at the center of the roll and cortical material is placed at the periphery of the roll to form an implant having a load bearing spiral structure with a fusion promoting core. For example, the bone pieces may be provided with varying load carrying capacity and fusion promoting properties to provide a gradient from a dense structural outer rim to a less dense fusion promoting core. For example, the implant may be arranged with long fully mineralized sticks of cortical bone near the perimeter, smaller and/or partially demineralized pieces closer to the center, cancellous and/or fully demineralized pieces at the center. The implant may also be arranged with a gradient of increasing mineralization from the center outwardly. It should be noted however, that any combination of biocompatible material, including cancellous and/or cortical bone as shown, in any shape, and/or bone growth promoting material, may be included at any position of the layered or rolled implants.

Figure 7:
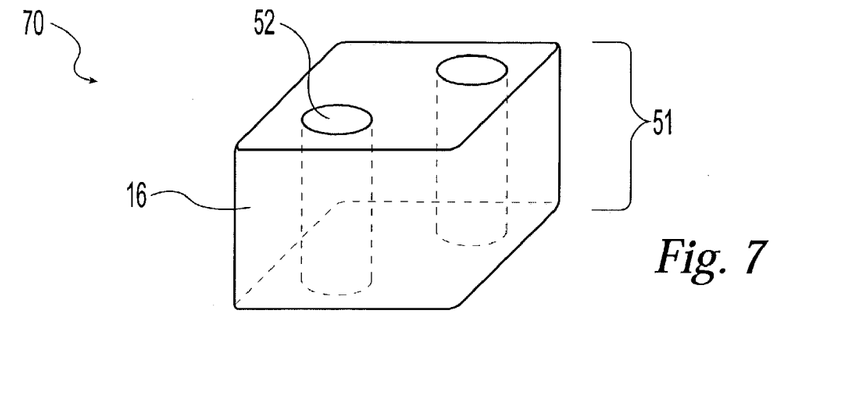
FIG. 7 is a perspective view of an implant like that of FIG. 1 shown with an additional structural member.
Figure 8:
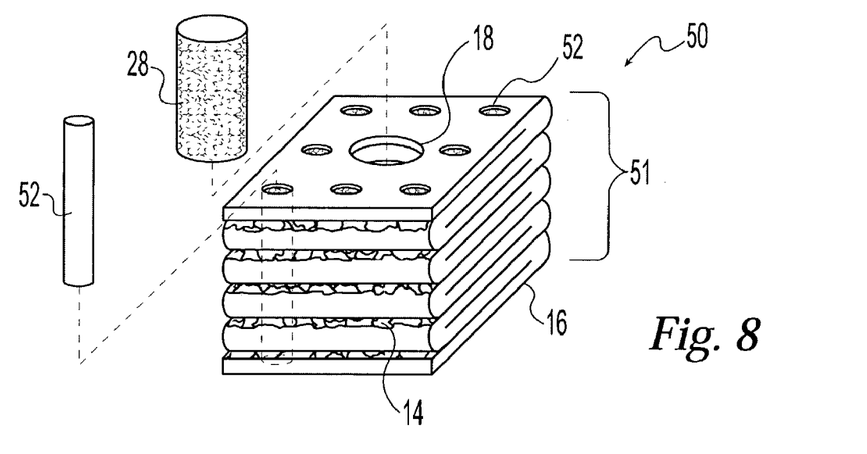
FIG. 8 is a perspective view of an implant like that of FIG. 7 showing a folded layer construction.

Referring to FIG. 7, another embodiment of a fusion implant 70 includes one or more layers 51 of one or more flexible planar members 16 and one or more structural members 52 affixed at a predetermined orientation within the layers of planar members. The predetermined orientation may be in alignment with a load bearing axis of the implant such that the positioning of the structural members 52 increase the load bearing capacity of the implant compared to the load bearing capacity of the layers 51 of planar members 16. For example, a relatively low load bearing capacity flexible planar member can retain a relatively high load bearing capacity structural member in an upright position between adjacent bony structures. In this construct, the retaining member may provide stability and space filling properties to a structural member that would otherwise be lacking a desired geometry to maintain its positioning. In the illustrative embodiment of FIG. 7, the flexible planar member 16 comprises a single, relatively thick layer. In the illustrative embodiment of FIG. 8, the flexible planar member comprises multiple layers formed by folding the flexible planar member 16 back on itself multiple times. The implant 50 and/or each layer may further include one or more openings 18, which may be filled with a bone growth promoting material 28 to facilitate fusion of adjacent bone through the implant. Additionally, structural members 52 may fix the plurality of layers of flexible planar members 16 relative to each other, and/or a securing mechanism 26 or additional adjoining flexible planar members 16 may be utilized to secure the relative position of the layers and shape of the implant. Optionally, additional material, such as bone pieces 14, may be positioned between the layers of flexible planar members 16 to increase load bearing capacity or enhance fusion through the implant.

Figure 9:
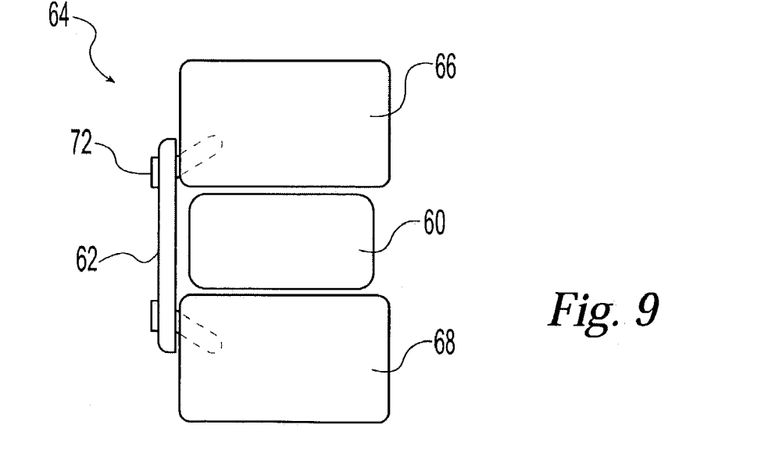
FIG. 9 is a side elevation view schematically showing an implant as in FIGS. 1-8 in combination with a supplemental fixation device.

Referring to FIG. 9, embodiments of a bone/flexible member fusion implant 60, such as those described above may be utilized in conjunction with a fixation device 62 to form a bone fixation system 64. In such a system 64, the fusion implant 60 is positioned between adjacent bony structures 66, 68 desired to be fused together. The fixation device 62 may include one or more anchor mechanisms 72, such as screws, pins, wires, and/or other mechanisms for attaching it to the adjacent bony structures 66, 68 to limit the relative motion between them. The fixation device 62 may substantially prevent all relative motion, or it may allow a predetermined amount of motion, such as to allow the implant 60 to remain in contact with the adjacent bony structures 66, 68 during the healing and fusion processes. Suitable examples of a fixation device 62 include plates, internal or external rod systems, cable systems, cerclage systems, screws, and other suitable devices and combinations thereof.

Structural members comprising cortical bone may have a predetermined layer thickness and geometry, measured radially from the longitudinal axis of the donor bone, less than a predetermined minimum wall thickness and geometry. For example, the predetermined layer thickness and geometry may be in the range of less than 2 mm thick in one embodiment, less than 1.8 mm thick in another embodiment, less than 1.5 mm thick in yet another embodiment, less than 1.0 mm thick in still another embodiment, and less than 0.5 mm thick in another embodiment. Further, for example, the predetermined minimum wall thickness and geometry may relate to a minimum acceptable thickness or geometry associated with forming an integral or assembled load bearing implant. The predetermined minimum cortical geometry may vary depending on the application. For example, a minimum geometry for use in the cervical spine may be substantially less than a minimum cortical geometry for the lumbar spine. For instance, a predetermined minimum wall thickness or geometry for integral or assembled cortical wedge cervical spine implant, such as may be formed from a fibula, may be 3.0 mm in one embodiment, 2.5 mm in another embodiment, 2.0 mm in yet another embodiment, and 1.8 mm in still another embodiment. On the other hand, a minimum cortical geometry for an integral or assembled lumbar implant may be 4.5 mm in one embodiment, 4.0 mm in another embodiment, and 3.5 mm in another embodiment.

Bone may be obtained from any suitable bone source including the implant recipient as in an autograft, another source of the same species as in an allograft, or a source of a different species as in a xenograft. Suitable examples of musculoskeletal tissue include ilium, humerus, tibia, femur, fibula, patella, ulna, radius, rib, vertebral bodies, and/or other suitable bones. The bone pieces may be machined, cut, planed, and/or otherwise removed and/or formed from the donor bone.

Implants formed from a plurality of bone pieces may have a compressive strength, or load bearing capacity, in the range of 50N to 20,000N. For instance, embodiments may have compressive strength greater than 70N, or greater than 800N, or greater than 1000N, or greater than 1200N, or greater than 3000N, or greater than 5000N, or greater than 7000N, or greater than 10,000N, or greater than 12,000N, or greater than 15,000N, or greater than 17,000N. This compressive strength provides load-bearing capability greater than typical cancellous bone and up to that of typical cortical bone.

Although embodiments of implants and methods of making implants have been described and illustrated in detail, it is to be understood that the same is intended by way of illustration and example only and is not to be taken by way of limitation. Accordingly, variations in and modifications to the implants and methods will be apparent to those of ordinary skill in the art, and the following claims are intended to cover all such modifications and equivalents.

What is claimed is:

1. An implant for use in fusing adjacent bony structures comprising at least one structural member combined with at least one flexible planar member forming a flexible outer layer wrapped around the at least one structural member to retain the at least one structural member to form the implant, and wherein said implant includes at least one opening extending continuously through the entire implant, said opening including an inner wall extending from a first surface of the implant for contacting a first one of said adjacent bony structures to a second surface of the implant for contacting a second one of said adjacent bony structures, said inner wall defined by portions of said flexible outer layer and of said at least one structural member.

2. The implant of claim 1 wherein the at least one structural member comprises at least one shape selected from the group consisting of particles, strips, blocks, and beams.

3. The implant of claim 1 wherein the at least one structural member comprises at least one material selected from the group consisting of bone, metal, ceramic, carbon and polymer.

4. The implant of claim 1 wherein the at least one structural member comprises at least one material selected from the group consisting of polyethylene, polyester, polyglycolic acid, polylactic acid, polytetrafluroethylene, polyaryletherketone, and polyetheretherketone.

5. The implant of claim 1 wherein the at least one flexible planar member comprises at least one shape selected from the group consisting of sheet, block, foam, woven fabric, non-woven fabric, membrane, and mesh.

6. The implant of claim 1 wherein the at least one flexible planar member comprises at least one material selected from the group consisting of body tissue, resorbable polymer, nonresorbable polymer, and metal.

7. The implant of claim 1 wherein the at least one flexible planar member comprises at least one material selected from the group consisting of fascia, skin, pericardium, partially demineralized bone, fully demineralized bone, cartilage, tendon, and ligament.

8. The implant of claim 1 wherein the flexible outer layer retains a plurality of structural members to maintain them in a predetermined form.

9. The implant of claim 1 wherein the structural member has a longitudinal axis and the flexible outer layer retains the structural member with its axis in a predetermined orientation.

10. The implant of claim 1 wherein the at least one structural member comprises a plurality of pieces of bone.

11. The implant of claim 10 wherein the individual pieces of bone have less than a predetermined minimum load bearing capacity and the combined pieces form an implant that achieves a predetermined capacity greater than the predetermined minimum load bearing capacity.

12. The implant of claim 11 wherein the individual pieces of bone have a predetermined geometry.

13. The implant of claim 12 wherein the individual pieces of bone comprise cortical bone harvested from a donor bone having a longitudinal axis, the individual pieces of bone having a thickness, measured radially from the longitudinal axis of the donor bone, less than 2 mm thick.

14. The implant of claim 10 wherein the pieces of bone include at least one shape selected from the group consisting of particles, strips, blocks, and beams.

15. The implant of claim 10 wherein the pieces of bone comprise cortical bone for achieving a predetermined load-bearing capability in the implant.

16. The implant of claim 15 wherein the pieces of bone further comprise cancellous bone.

17. The implant of claim 16 wherein the individual pieces of bone are further interconnected by at least one means selected from the group consisting of chemical and mechanical means.

18. The implant of claim 17 wherein the individual pieces of bone are interconnected by at least one means selected from the group consisting of pinning, suturing, pressing, incorporating a binding agent, collagen crosslinking, and interlocking mechanical engagement.

19. The implant of claim 18 wherein the individual pieces of bone are interconnected with at least one material selected from the group consisting of fibrin glue, cyanoacrylate, epoxy, polymethylmethacrylate, and gelatin.

20. The implant of claim 10 wherein the at least one flexible planar member comprises at least one shape selected from the group consisting of sheet, block, foam, woven fabric, non-woven fabric, membrane, and mesh.

21. The implant of claim 10 wherein the at least one flexible planar member comprises at least one material selected from the group consisting of body tissue, resorbable polymer, nonresorbable polymer, and metal.

22. The implant of claim 10 wherein the at least one flexible planar member comprises at least one material selected from the group consisting of fascia, annular fibrosus, skin, pericardium, partially demineralized bone, fully demineralized bone, cartilage, tendon, and ligament.

23. The implant of claim 10 wherein the flexible planar member further comprises different types of elongated, planar material.

24. The implant of claim 23 wherein one type of planar material is utilized in one dimension while a different type of planar material is utilized in another dimension.

25. The implant of claim 10 wherein the flexible outer layer retains the bone pieces in a predetermined form.

26. The implant of claim 25 wherein the predetermined form comprises at least one form selected from the group consisting of substantially rectangular prisms, spheres, and hemispheres, and combinations thereof.

27. The implant of claim 10 wherein the flexible outer layer and said plurality of pieces of bone combine to provide a load bearing implant body sized and configured for insertion between adjacent first and second vertebrae.

28. The implant of claim 27 wherein the at least one opening is sized such that it is smaller than the bone pieces such that the bone pieces are contained by the flexible outer layer.

29. The implant of claim 27 wherein a retaining material is inserted within the at least one opening to bind with the pieces of bone to retain them within the at least one opening.

30. The implant of claim 29 wherein the retaining material comprises at least one material selected from the group consisting of bone paste, collagen, gelatin, polymers, fibrin, and settable ceramics.

31. The implant of claim 27 wherein the flexible planar member comprises a plurality of layers with the bone pieces being positioned between the layers.

32. The implant of claim 27 wherein the at least one opening comprises an inner wall extending through the entire implant from a first implant surface configured to contact the first vertebra to a second implant surface configured to contact the second vertebra.

33. The implant of claim 32 wherein the inner wall is formed through a first layer of the flexible outer layer, through the bone pieces and through a second layer of the flexible outer layer.

34. The implant of claim 32 wherein the opening and inner wall are formed by at least one operation selected from the group consisting of drilling, cutting, and punching.

35. The implant of claim 32 wherein the opening and inner wall comprise a hollow member having a wall defining the opening and inner wall.

36. The implant of claim 35 wherein the hollow member comprises at least one biocompatible material capable of preventing the passage of the bone pieces through its structure.

37. The implant of claim 27 further comprising a bone growth-promoting material inserted within the at least one opening.

38. The implant of claim 37 wherein the bone growth-promoting material comprises at least one material selected from the group consisting of bone paste, cancellous bone, bone chips, bone morphogenic protein (BMP), LIM mineralization protein (LMP), platelet derived growth factors, bone marrow aspirate, stem cells, biologic growth factors, and combinations thereof.

39. The implant of claim 10 further comprising a securing mechanism to insure that the flexible outer layer maintains a bone-retaining position.

40. The implant of claim 39 wherein the securing mechanism attaches one portion of the flexible outer layer to another portion of the flexible outer layer.

41. The implant of claim 39 wherein the securing mechanism comprises at least one mechanism selected from the group consisting of sutures, wires, pins, straps, clamps, staples, heat bonding, cross-linking, ultrasonic welding, and adhesives.

42. The implant of claim 39 wherein the securing mechanism connects a plurality of implants to form a larger implant.

43. The implant of claim 39 wherein the securing mechanism comprises a material that resorbs within the body after a predetermined period of time.

44. The implant of claim 10 wherein the bone pieces and flexible planar member form a plurality of layers.

45. The implant of claim 44 wherein the flexible outer layer completely encompasses the bone pieces except at said at least one opening.

46. The implant of claim 45 wherein the implant comprises cancellous bone pieces and cortical bone pieces rolled up within at least one flexible planar member.

47. The implant of claim 46 wherein the cancellous bone pieces are located near the center of the roll and the cortical bone pieces are located near the periphery of the roll.

48. The implant of claim 44 wherein the layers are oriented in an orientation selected form the group consisting of substantially horizontal, substantially vertical, substantially curvilinear, and substantially planar.

49. The implant of claim 44 wherein at least one layer primarily provides structural support and at least one layer primarily provides a bone fusion material.

50. The implant of claim 49 wherein the at least one structural support layer comprises cortical bone and the at least one fusion layer comprises cancellous bone.

51. The implant of claim 44 wherein the layers are formed radially relative to a center of the implant, the bone pieces comprising a plurality of bone pieces with differing load carrying capacity, the bone pieces being arranged in the radial layers with bone pieces having lower load carrying capacity nearer the center and bone pieces with higher load carrying capacity further from the center.

52. The implant of claim 44 wherein at least one layer of said plurality of layers comprises exposed bone at an edge to promote fusion of adjacent bony structures through the layer.

53. The implant of claim 9 wherein the at least one flexible planar member comprises a plurality of layers and the at least one structural member is positioned in at least one opening through the layers.

54. The implant of claim 53 wherein the at least one structural member is positioned substantially normal to the at least one planar member.

55. The implant of claim 9, wherein said at least one structural member comprises a plurality of pieces of bone.

56. The implant of claim 55 further comprising a bone growth promoting material within the at least one opening.

57. The implant of claim 53 wherein the at least one structural member fixes the plurality of layers of flexible planar members relative to each other.

58. The implant of claim 53 wherein at least one layer of bone pieces is positioned between the layers of flexible planar members.

59. The implant of claim 9 wherein the at least one structural member comprises a biocompatible material capable of withstanding a predetermined load.

60. The implant of claim 59 wherein the at least one structural member comprises at least one structure selected from the group consisting of bone members, polymer members, resorbable polymer members, and combinations thereof.

61. The implant of claim 59 wherein the at least one structural member comprises at least one material selected from the group consisting of polyethylene, polyester, polytetrafluroethylene, polyaryletherketone, polyetheretherketone, polylactic acid, polyglycolic acid, carbon, and combinations thereof.

62. The implant of claim 1 further comprising a fixation device attached to said adjacent bony structures to limit the relative motion between them.

63. The implant of claim 62 wherein the fixation device substantially prevents all relative motion between the adjacent bony structures.

64. The implant of claim 62 wherein the fixation device allows a predetermined amount of relative motion between the adjacent bony structures during the fusion process.

65. The implant of claim 62 wherein the fixation device is selected from the group consisting of plates, internal or external rod systems, cable systems, cerclage systems, screws, and combinations thereof.

66. A load bearing implant for use in fusing adjacent bony structures comprising: a plurality of bone pieces; and a flexible outer layer formed with at least one flexible planar member, the flexible outer layer wrapped around and containing the bone pieces; and said implant having a compressed spherical form substantially similar to the shape of a human spinal disc, and wherein the flexible planar member includes at least one opening to permit fusion of the adjacent bony structures through the implant, said opening including an inner wall extending from a first surface of the implant for contacting a first one of said adjacent bony structures to a second surface of the implant for contacting a second one of said adjacent bony structures, said inner wall defined by portions of said flexible planar member and of said bone pieces.

67. The implant of claim 66 wherein the bone pieces comprise cortical bone.

68. A load bearing implant for use in fusing adjacent bony structures comprising:
load bearing means for supporting said adjacent bony structure in spaced relationship;
retaining means for retaining the load bearing means in a predetermined orientation, said retaining means wrapped around said load bearing means; and said implant including at least one opening extending continuously through the entire implant, said opening including an inner wall extending from a first surface of the implant for contacting a first one of said adjacent bony structures to a second surface of the implant for contacting a second one of said adjacent bony structures, said inner wall defined by portion of said retaining means and of said load bearing means.

69. A system for use in fusing adjacent bony structures, comprising:
a plurality of bone pieces;
at least one flexible planar member forming a flexible outer layer wrapped around and substantially retaining the plurality of bone pieces;
said plurality of bone pieces and flexible outer layer incorporated in an implant having at least one opening extending continuously through the entire implant; said opening including an inner wall extending from a first surface of the implant for contacting a first one of said adjacent bony structures to a second surface of the implant for contacting a second one of said adjacent bony structures, said inner wall defined by portions of said flexible layer and of said plurality of bone pieces; and
a fixation device attachable to the adjacent bony structures and having a structure to limit relative motion between the adjacent bony structures.

70. An implant for use in fusing adjacent bony structures comprising:
at least one retaining member having a first load carrying capacity;
at least one structural member having a second load carrying capacity greater than the first load bearing capacity, the retaining member wrapped around and retaining the structural member in a predetermined orientation relative to the adjacent bony structures; and
said implant having at least one opening extending continuously through the entire implant, said opening including an inner wall extending from a first surface of the implant for contacting a first one of said adjacent bony structures to a second surface of the implant for contacting a second one of said adjacent bony structures, said inner wall defined by portions of said at least one retaining member and of said at least one structural member.

71. An implant for use in fusing adjacent bony structures comprising at least one structural member combined with at least one flexible planar member forming a flexible outer layer wrapped around and retaining the at least one structural member to form the implant, wherein the at least one structural member comprises a plurality of pieces of bone, wherein the implant further comprises at least one opening to permit fusion of the adjacent bony structures through the implant, and wherein the at least one opening comprises an inner wall extending through the entire implant.

72. The implant of claim 71 wherein the opening and inner wall are formed by at least one operation selected from the group consisting of drilling, cutting, and punching.

73. The implant of claim 71 wherein the opening and inner wall comprise a hollow member having a wall defining the opening and inner wall.

* * * * *